United States Patent [19]

Röckseisen

[11] Patent Number: 5,657,368
[45] Date of Patent: Aug. 12, 1997

[54] APPARATUS FOR POSITIONING AND MARKING A PATIENT AT A DIAGNOSTIC APPARATUS

[75] Inventor: Armin Röckseisen, Scharnebeck, Germany

[73] Assignee: Lap GmbH Laser Applikationen, Luneburg, Germany

[21] Appl. No.: 488,581

[22] Filed: Jun. 8, 1995

[51] Int. Cl.$^6$ ............................................. A61B 6/08
[52] U.S. Cl. ................................. 378/206; 378/205
[58] Field of Search ................................. 378/205, 206, 378/62, 63, 64, 65

[56] References Cited

U.S. PATENT DOCUMENTS

| | | | |
|---|---|---|---|
| 4,242,587 | 12/1980 | Lescrenier | 378/206 |
| 4,293,771 | 10/1981 | Lescrenier | 378/206 |
| 5,206,893 | 4/1993 | Hara | 378/206 |

*Primary Examiner*—Don Wong
*Attorney, Agent, or Firm*—Vidas Arrett & Steinkraus, P.A.

[57] ABSTRACT

An apparatus for positioning and marking a patient at a diagnostic apparatus, for example before and after being scanned in a computer tomograph, comprising at least four line lasers adapted to be displaced along an axis, two of said line lasers being arranged above the patient lying upon a displaceable bed so as to project a sagittal line and a transversal line onto the body of the patient and two of said line lasers being arranged laterally of the bed so as to project a line along the body axis laterally onto the body, numerically controlled drives for said line lasers for adjustment thereof transversely to the respective projected lines, position control means for said drives, and manually operable input means for said control means for entering coordinates related to the position and extent of an area to be irradiated and determined by the computer tomograph.

2 Claims, 2 Drawing Sheets

APPARATUS FOR POSITIONING AND MARKING A PATIENT AT A DIAGNOSTIC APPARATUS

SUMMARY OF THE INVENTION

The present invention relates to an apparatus for positioning and marking a patient at a diagnostic apparatus, for example prior and after having been transilluminated in a computer tomograph.

In radiation therapy it is necessary to direct the beam of the radiation source precisely onto the patient body zone to be irradiated, and this in a reproducible manner. For reducing the strain on zones not to be treated the radiation source is pivoted about a so-called isocenter so that the center of the zone to be irradiated receives always the same treatment dose while the adjacent zones not to be treated receive a substantially reduced treatment loading. Positioning of a patient with respect to the radiation apparatus is to be performed such that the center of the zone to be irradiated coincides with the isocenter of the radiation apparatus. The position of the zone to be irradiated may be determined by suitable diagnostic methods, for example by means of a computer tomograph (CT). In this connection it is not only the coordinates of the center of the zone to be irradiated that is important, but also the extent and the circumference of the zone which is to be covered by the radiation apparatus. The focus of the irradiation zone usually is between the radiation source and the body of the patient. This results in a divergent radiation which covers a more or less substantial surface on the skin depending on the dimensions of the body of the patient. By means of respective marking thereof, it is possible to reduce this surface.

In order to orient the patient with respect to the radiation apparatus, it is necessary to indicate and mark the position of the zone to be irradiated. It has become known to move the patient by means of a line laser system fixedly positioned in the irradiation space to a precise position before the patient is moved into the radiation apparatus.

The coordinates of the zone to be irradiated are determined by means of for example a computer tomograph. The coordinates will be marked on the skin of the body of the patient such that the center of the tumor is in the isocenter of the radiation apparatus when the patient is aligned to the radiation apparatus.

It is an object of the invention to provide an apparatus for positioning and marking a patient by means of a computer tomograph.

The invention is defined in patent claim 1.

The apparatus of the invention provides at least four line lasers which are arranged in space so as to be displaceable along an axis. At least two laser units disposed above the patient generate a so-called sagittal line and a so-called transversal line. Preferrably, two line lasers are used for generating a common transversal line which approximately extends about the body. Displacing the line laser allows for example to displace the transversal line along the sagittal axis while the transversal line can be moved along the transversal axis. Two further laser units each project a line along the body axis laterally upon the body. They can be moved synchronously up and down under a right angle to the above mentioned axes. The above mentioned lines are boundaries of light planes which originate from the laser units. The beam planes intersect each other in a point of an orthogonal coordinate system. In the desired marking of a zone to be irradiated the origin of the coordinate system is to coincide with the center of the zone to be irradiated so that this center coincides with the isocenter of the radiation apparatus.

The position control means controls the numeric drives for the laser units in order to effect the desired movements. The rate of movement depends on control data which are entered into the control means by means of a manually operable input device. These data will be determined by means of the diagnostic apparatus, for example a computer tomograph. By means of the computer tomograph the coordinates of the center of the zone to be irradiated (tumor center) can be determined. As an alternative, the coordinates of the extent of the tumor along the three axes can be determined. When these coordinates are known, they can be entered into the control means via the input device, and the control means moves the projected lines to the desired positions. Further data additional to the coordinates of the tumor can be entered, namely the divergents of the radiation apparatus. This characteristic determines the irradiated skin surface or the irradiated surface of the tumor. This surface is also dependent on the spacing between the skin and focus of the radiation apparatus. As a result displacing the lines to the desired positions allows to determine not only the isocenter of the irradiation, but also for example the perpendicular projection of the geometric extent of the tumor on the skin surface along the three axes. Furthermore, it is possible to determine and mark the entry field boundaries in the distance between the focus and skin as well as arbitrary other positions in accordance with the input of specific coordinates.

Due to use of a separate input device the apparatus of the present invention is fully independent of the respective design of the computer tomograph or a similar diagnostic apparatus. The invention will be explained in more detail with reference to drawings.

DETAILED DESCRIPTION OF THE PREFERRED EMBODIMENT

Figure 1:
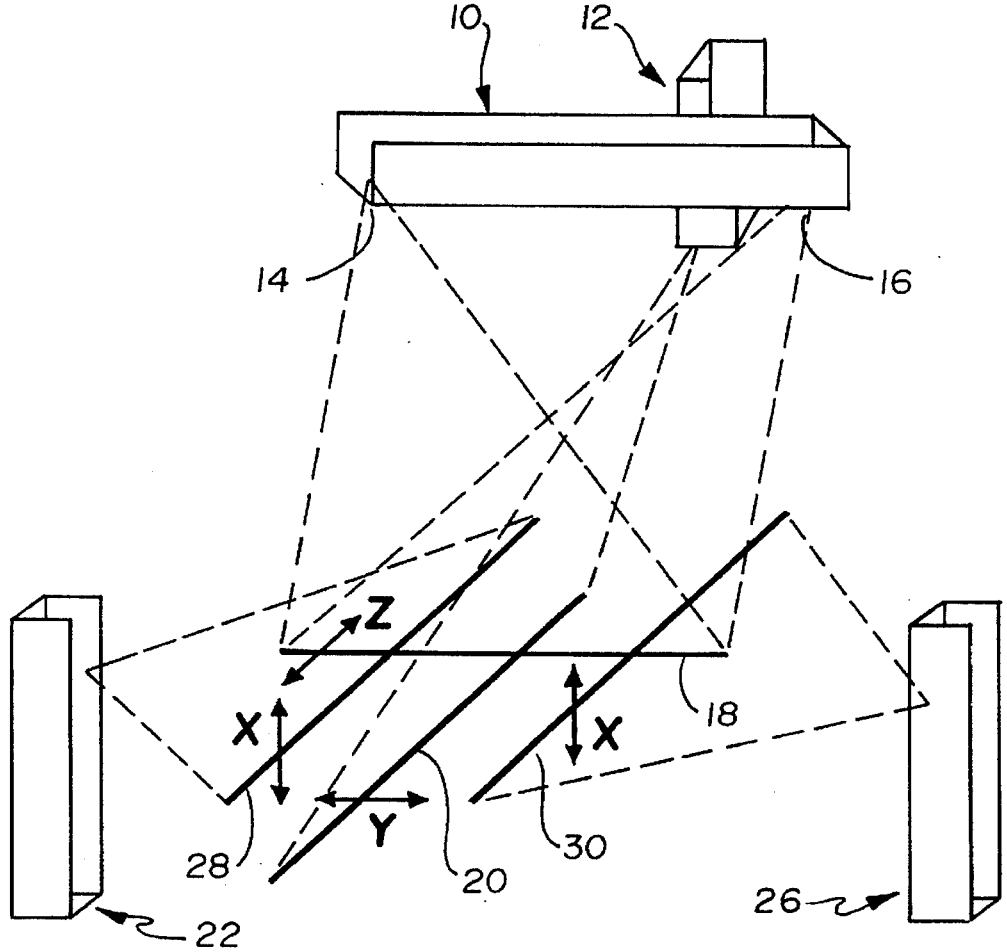
FIG. 1 shows very schematically a part of an apparatus of the invention.

FIG. 1 shows two laser units 10, 12 which are mounted to the ceiling of a room. Furthermore, the room contains a computer tomograph (44') as well as a displaceable 46' for a patient for transporting the patient into and from the computer tomograph 44' with the table 46 being displaceable also by means of a numerically controlled drive 42. The laser unit 10 includes a pair of lasers 14, 16 for generating a common transversal line 18 which extends substantially about the not shown body of the patient.

The laser unit 12 generates a sagittal line which allows to align the patient on the table 46 to this line. A pair of lateral laser units 22, 26 each project a line along the body axis laterally onto the body. These lines are designated by 28 and 30, respectively.

The laser units 10, 12, 22 and 26 are arranged to be displaceable along an axis by means of numerically controlled drives (34, 36, 38 and 40') such that the transversal line 18 is displaceable along the sagittal axis (Z-axis), the sagittal line 20 is displaceable along the transversal axis (Y-axis) and the lateral lines 28, 30 are displaceable along the X-axis.

The planes which include the above mentioned lines 18, 20, 28 and 30 intersect each other in an origin of the coordinate system which can be displaced by displacing the laser units 10, 12, 22, and 26' just as individual lines can be displaced.

Figure 2:
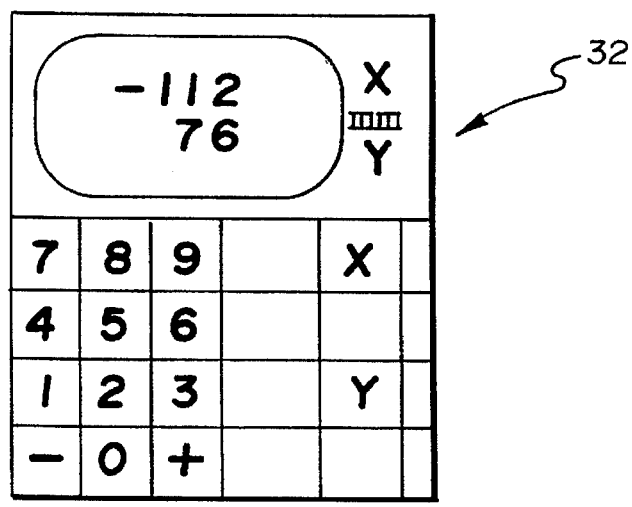
FIG. 2 shows schematically the input unit for control means for the apparatus of the invention.
Figure 3:
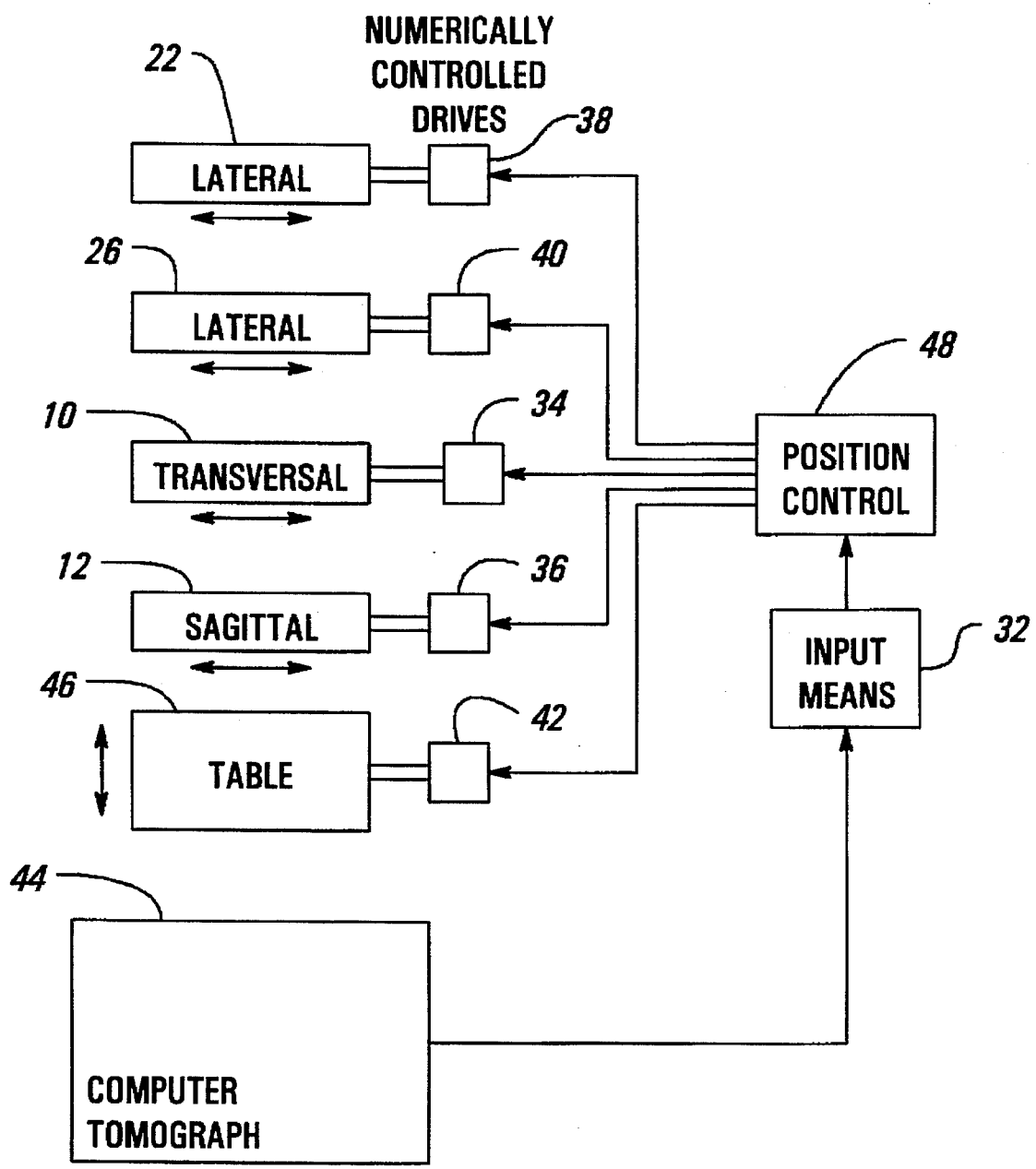
FIG. 3 is a block diagram showing the structuer of an embodiment of the present invention.

The drives 34, 36, 38, 40, and 42 are controlled by a positioning control means 48' which receives command data from an input device 32 (FIG. 2) comprising a keyboard which is shown in FIG. 2.

In the following the sequence of operation of the apparatus of FIGS. 1 and 2 will be explained. In the original condition the sagittal laser 12 is in the center while the two lateral lines 28, 30 are in a defined origin. The transversal line 18 extends so as to have a defined spacing from the transverse axis of the computer tomograph 44'. As already mentioned the laser lines intersect each other in a virtual isocenter. The patient can be orientated in accordance with these lines and can be transported to the computer tomograph 44'. After the diagnosis operation the position and the extent of the tumor have been determined. Thereafter the patient on the table 46' will be moved with the assistance of the control of the computer tomograph 44' so far that the center of the tumor is in the plane of the transversal line 18. The two other coordinates of the tumor center (X and Y) are determined from the result of the computer tomograph 44' and are entered manually into the input device 32 whereby the laser lines 20, 28, 30 are moved to the indicated positions. The three-dimensional net of coordinates of laser lines projected now upon the body of the patient indicates the position of the center of the tumor which can be transferred onto the patient by marking in order to provide for a reproduciable positioning thereof with respect to the isocenter of the radiation apparatus.

Entering further parameters or coordinates allows to displace the lines so as to indicate the geometrical extent of the tumor on the skin. Of interest are on the one hand the extent of the tumor in the vertical section plane of the computer tomograph (projection of the geometrical data onto the skin surface) and the field of entry of the radiation which is determined by the divergence of the radiation apparatus and the spacing between the focus and the skin. The control computer uses these entered data of the coordinates and the parameters of the radiation apparatus (divergence and spacing) to determine the positions to be indicated. The lines imaged on the skin will be used for further marking of the patient.

We claim:

1. An apparatus for positioning and marking a patient at a diagnostic apparatus, comprising a computer tomograph;

at least four beam generating lasers, each laser beam producing a line on a surface impinged, the lasers being adapted to be displaced along an axis, two of said lasers being arranged above a displaceable table for a patient lying thereupon so as to project a sagittal line and a transversal line onto the body of the patient, and two of said lasers being arranged laterally of said table so as to project a line along the body axis laterally onto the body;

a numerically controlled drive means for said lasers adapted to move said lasers along said axes, each of said axes extends transversely to the respective projected line, a numerically controlled drive means for said table;

a position control means for said drives, and manually operable input means for said control means for entering coordinates related to the position and extent of an area to be irradiated and determined by said computer tomograph, said control means controlling displacement of said table such that the transversal line extends through said area and the displacement of said lasers providing said sagittal line and said lateral lines such that they extend through said area.

2. An apparatus as defined in claim 1, further comprising a fifth laser, the fifth laser being arranged above the table and wherein said transversal line is generated by a pair of the lasers above the table.

* * * * *